United States Patent
Babson

(10) Patent No.: US 9,366,662 B2
(45) Date of Patent: Jun. 14, 2016

(54) SERUM SAMPLE QUALITY DETERMINATION

(71) Applicant: Arthur Babson, Chester, NJ (US)

(72) Inventor: Arthur Babson, Chester, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/405,571

(22) PCT Filed: Jun. 4, 2013

(86) PCT No.: PCT/US2013/044005
§ 371 (c)(1),
(2) Date: Dec. 4, 2014

(87) PCT Pub. No.: WO2013/184625
PCT Pub. Date: Dec. 12, 2013

(65) Prior Publication Data
US 2015/0168371 A1  Jun. 18, 2015

Related U.S. Application Data

(60) Provisional application No. 61/655,703, filed on Jun. 4, 2013.

(51) Int. Cl.
*G01N 33/48* (2006.01)
*G01N 33/49* (2006.01)
(Continued)

(52) U.S. Cl.
CPC ............... *G01N 33/49* (2013.01); *G01N 21/31* (2013.01); *G01N 21/51* (2013.01);
(Continued)

(58) Field of Classification Search
CPC .............. G01N 2021/8535; G01N 2021/8542; G01N 2021/8514; G01N 21/51; G01N 21/8507
See application file for complete search history.

(56) References Cited

U.S. PATENT DOCUMENTS 5,279,793 A * 1/1994 Glass .................. G01N 13/04
                                                250/227.14
6,388,750 B1 * 5/2002 Liu ..................... G01F 23/292
                                                356/246

(Continued)

OTHER PUBLICATIONS

PCT International Search Report and Written Opinion dated Oct. 25, 2013 (9 Pages).

*Primary Examiner* — Kara E Geisel
*Assistant Examiner* — Shawn Decenzo
(74) *Attorney, Agent, or Firm* — Preti, Flaherty, Beliveau & Pachios LLP

(57) ABSTRACT

A method and device for measuring HIL levels in blood serum samples that are disposed in an automated, clinical chemistry analyzer. The device probe can be attached adjacent to a pipette or sample probe of the analyzer and includes fiber optic bundles and a light-reflecting surface. A cutaway portion is provided between the ends of each of the fiber optic bundles and the light-reflecting surface. One of the four fiber optic bundles is optically coupled to a light-emitting source. Each of the other three fiber optic bundles collects and filters reflected light from the reflecting surface. The light filters correspond to the optimal absorption wavelengths for one of hemoglobin, bilirubin, and triglycerides. A light intensity-measuring device is optically coupled to each of the three fiber optic bundles, to measure the intensity of the filtered, reflected light. A processing device receives output data signal from the light intensity-measuring devices; stores the data; and calculates whether a serum sample has elevated levels of one or more of HIL.

21 Claims, 2 Drawing Sheets

(51) Int. Cl.
  *G01N 21/31* (2006.01)
  *G01N 21/85* (2006.01)
  *G01N 21/51* (2006.01)

(52) U.S. Cl.
  CPC ... *G01N 21/8507* (2013.01); *G01N 2021/3137* (2013.01); *G01N 2021/3148* (2013.01); *G01N 2021/8535* (2013.01)

(56) References Cited

U.S. PATENT DOCUMENTS

| | | | |
|---|---|---|---|
| 6,818,435 B2 | 11/2004 | Carvalho et al. | |
| 7,324,203 B2 * | 1/2008 | Ho | F23N 5/082 356/432 |
| 7,651,868 B2 | 1/2010 | McDevitt et al. | |
| 8,088,593 B2 | 1/2012 | Burd et al. | |
| 2009/0068668 A1 | 3/2009 | Duer | |
| 2010/0042005 A1 * | 2/2010 | Bigio | G01N 21/59 600/476 |
| 2010/0267049 A1 | 10/2010 | Rutter et al. | |
| 2012/0129269 A1 * | 5/2012 | Choi | A61B 5/0075 436/164 |
| 2012/0231488 A1 * | 9/2012 | Marshall | B01L 3/502715 435/29 |

\* cited by examiner

SERUM SAMPLE QUALITY DETERMINATION

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Blood serum samples are frequently assayed on automated, clinical chemistry analyzers. Problematically, elevated levels of hemoglobin (hemolysis), bilirubin (icterus), and/or triglycerides (lipemia), which are commonly referred to by the acronym HIL, can compromise the accuracy of the analysis. Thus, it would be desirable to identify serum samples having HIL problems in advance before further analysis is performed.

Currently, automated, clinical chemical analyzers such as those manufactured by Siemens Healthcare Diagnostics of Glasgow, Del. ("Siemens"), e.g., the Dimension Vista®, are adapted to measure HIL levels before further analysis. The Siemens analyzers, first, aspirate, e.g., using a pipette, an additional serum sample from the sample vessel and dispose the aspirated sample into a second cuvette along with a diluent. The second cuvette containing the aspirated serum sample and diluent is then transported to a photometer.

The photometer measures the absorbance of the aspirated sample in the second sample vessel. To check for elevated levels of each of the hemoglobin, bilirubin, and triglycerides, the serum sample is subject to a photometer(s) capable of measuring at three different wavelengths of light. Advantageously, it would be desirable to bring the photometer to the serum sample in the sample vessel rather than vice versa, to minimize spillage and possible contamination of the analyzer. More advantageously, it would be desirable to provide a photometer that can test for elevated levels of hemoglobin, bilirubin, and triglycerides simultaneously.

BRIEF SUMMARY OF THE INVENTION

A device for measuring HIL levels in blood serum samples that are disposed in an automated, clinical chemistry analyzer as well as methods of determining elevated HIL levels and of determining elevated levels of HIL in blood serum samples using the device are disclosed. Advantageously, the device is inexpensive, can be easily incorporated into existing, commercially-available analyzers, and can be easily (automatically) washed between samples.

The device is a test or measuring probe that can be a stand alone apparatus or attached adjacent to the pipette probe of the analyzer. In either embodiment, the test or measuring probe includes a plurality of fiber optic bundles and a light-reflecting surface, e.g., a mirror. The light-reflecting surface is disposed at a distal end of the test or measuring probe at some desirable distance from the ends of the fiber optic bundles. A cutaway portion is provided between the ends of each of the plurality of fiber optic bundles and the light-reflecting surface.

The plurality of fiber optic bundles can be four in number. One of the four fiber optic bundles is optically coupled to a light-emitting source that is adapted to generate light into the blood serum sample contained in the cut-away portion towards the reflecting surface. Each of the other three fiber optic bundles is adapted to collect reflected light from the light-reflecting surface and to filter the reflected light. Each of the light filters coupled to corresponding fiber optic bundles can be a monochromatic or band-pass-type filter, whose band-pass range corresponds to the optimal absorption wavelengths for one of hemoglobin, bilirubin, and triglycerides.

A light intensity-measuring device, e.g., a photodiode, a phototube, a photomultiplier tube, and the like, is optically coupled to each of the fiber optic bundles after the filter. The light intensity-measuring devices are adapted to measure the intensity of the filtered reflected light and to output a corresponding data signal to a processing device. The processing device receives the output data signal; stores the data as required; and calculates whether or not a discrete blood serum sample has elevated levels of one or more constituents of HIL. Blood serum samples with elevated levels of HIL can be flagged or removed from the analyzer automatically or manually.

During operation of the device, the tip of the test or measuring probe is inserted into and/or immersed in the serum sample so that some of the blood serum enters and fills the cutaway portion. The light-emitting source optically coupled to one of the fiber optic bundles emits light, which exits the end of the fiber optic bundles and travels through a fixed path length of the cutaway portion before the incident light is reflected by the light-reflecting surface. Each of the other three fiber optic bundles collects the reflected light and filters the light at a discrete wavelength. A light-intensity measuring device measures the intensity of the filtered light; and generates output data signals. The processing device receives the output data signals and compares them to acceptable levels of HIL.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

A device for measuring HIL levels in blood serum samples that are disposed in sample vessels of an automated, clinical chemistry analyzer will now be described. Automated, clinical chemical analyzers are well-known to those of ordinary skill in the art and will not be described in detail. For the purpose of illustration and not limitation, an embodiment of the invention will be described that co-locates a HIL-measuring device with the pipette or sample probe of the analyzer. Those of ordinary skill in the art can appreciate that the HIL-measuring device can also be a stand alone device having its own robotic arm and ancillary equipment.

Figure 1:
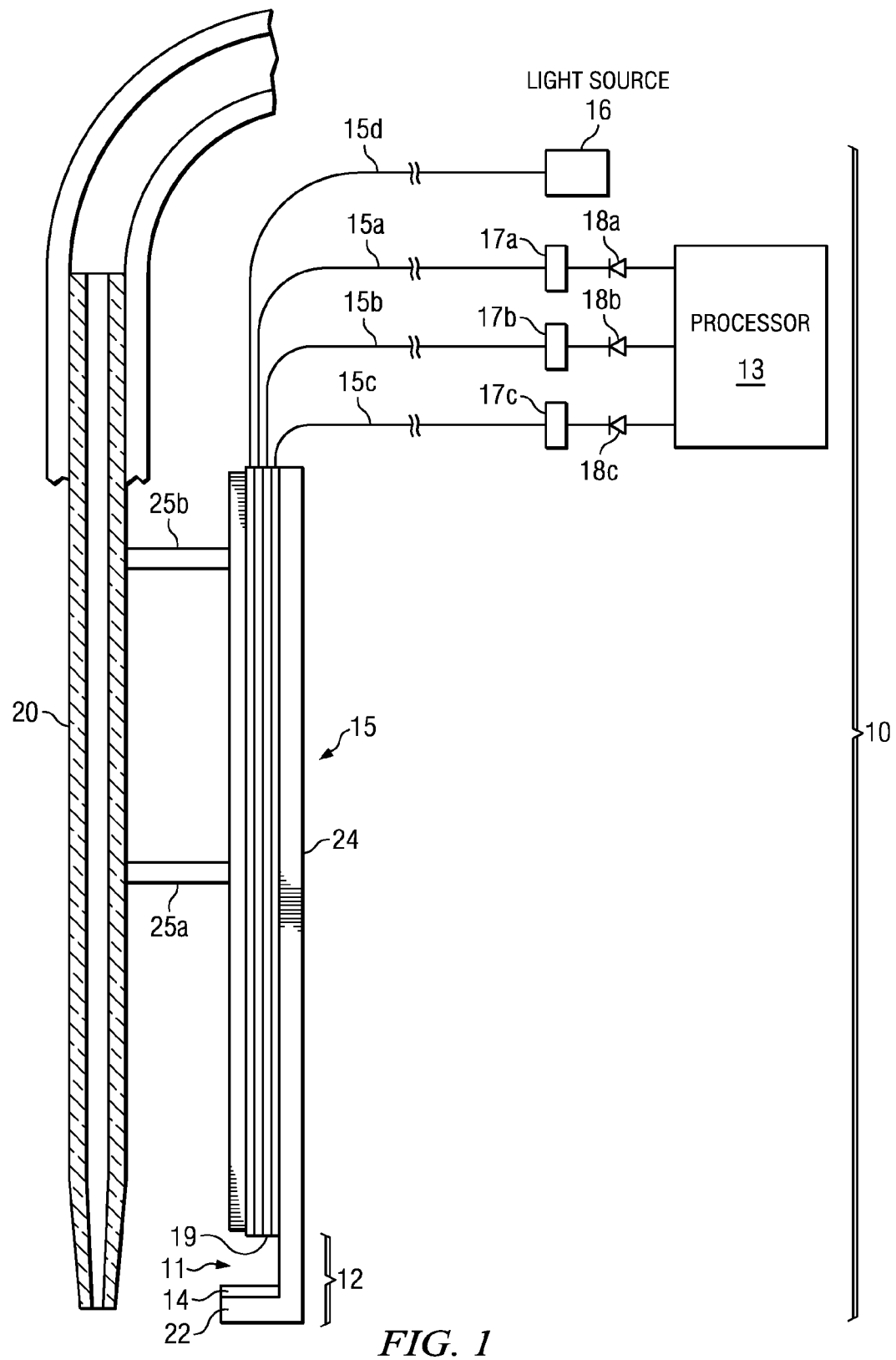
FIG. 1 shows a schematic view of an HIL-measuring device disposed adjacent to a pipette probe in accordance with the invention as claimed.
Figure 2:
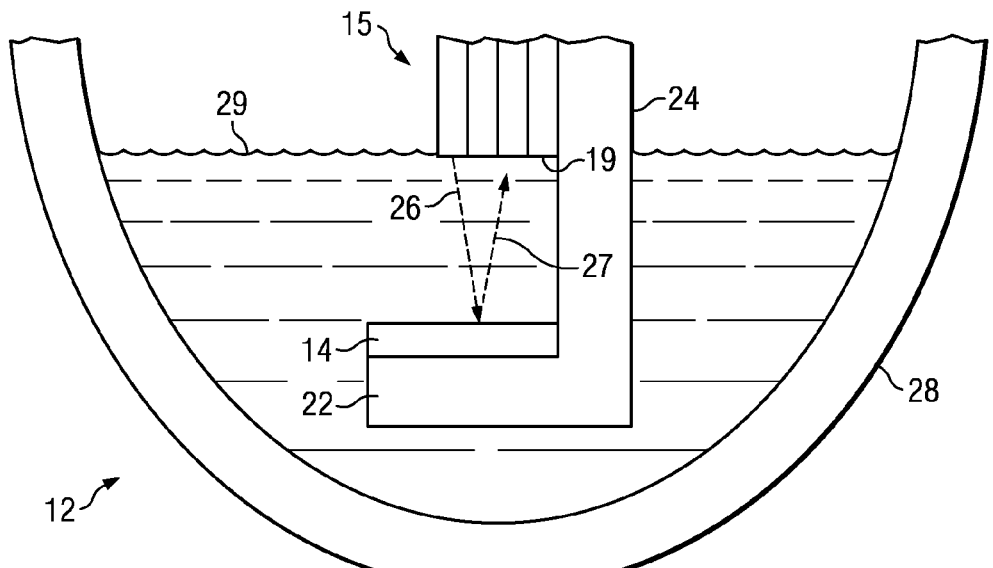
FIG. 2 shows a schematic detail of the tip of the HIL-measuring device of FIG. 1 immersed in a vessel containing a blood serum sample.

Referring to FIG. 1 and FIG. 2, the pipette or sample probe 20 of a chemical analyzer (not shown) is shown. As is well known to the art, pipettes or sample probes 20 are typically attached to robotic arms and positioned at discrete working locations. Pipettes or sample probes 20 are adapted to introduce a liquid, e.g., a diluent, a reactant, a base, and so forth, into a sample vessel 28 and/or to aspirate a measured volume of the liquid sample from the sample vessel 28.

The HIL-measuring device 10 is a test or measuring probe that can be fixedly or removably attached adjacent to the pipette or sample probe 20 of the analyzer. The proximity of the two probes 10, 20 should be close enough so that both probes 10, 20 can be introduced into a common sample vessel 28 simultaneously. Advantageously, the proximity of the two probes 10, 20 facilitates a single washing operation and a single washing station, to clean both the pipette or sample probe 20 and the HIL-measuring device 10.

Were the HIL-measuring device 10 a stand alone test or measuring probe, a separate robotic arm would be required and separate washing operations would be necessary. Advantageously, though, the tip 12 of the HIL-measuring device 10 and that of the pipette or sample probe 20 would not have to be simultaneously inserted into a common, crowded sample vessel 28.

The test or measuring probe 10 includes a support portion 24 having an L-projection 22 at a distal end. The support portion 24 and L-projection 22 can be manufactured from a single element or can be joined elements. In order to accommodate liquid level-sensing by conductance and/or capacitance, the element(s) should be manufactured of a conductive plastic or a conductive metal.

The elongate, vertical or near vertical support portion 24 is structured and arranged to support a plurality of fiber optic bundles 15 while the horizontally-disposed L-projection is structured and arranged to support a light-reflecting surface 14, e.g., a mirror.

An open, cutaway portion 11 is provided between the ends 19 of each of the plurality of fiber optic bundles 15 and the top surface of the light-reflecting surface 14. The cutaway portion 11 can be coated or treated with a hydrophilic material to ensure that the serum being sampled enters into the cutaway portion 11. Any material that ensures that the serum completely fills the cavity of the cutaway portion 11 can be used. What is important is that the serum completely fills the cutaway portion 11. When it does not, the light path will effectively be shorter and the absorbed light will be reduced, resulting in faulty HIL measurements. The preferred dimensions of the cutaway portion 11 and the cutaway area—on the order of a few millimeters—would be determined based on the light path necessary for adequate and acceptable sensitivity for all three of the HIL measurements.

At least one support spacer 25a, 25b is provided to support the test or measuring probe 10 from the pipette or sample probe 20 and to maintain the test or measuring probe 10 in vertical or substantially vertical orientation. The support spacer(s) 25a, 25b is fixedly or removably attached to the support portion 24 and, to facilitate removal of the probe 10 from the pipette or sample probe 20, removably attached to the pipette and/or sample probe 20. The support spacer 25a disposed closest to the probe tip 12 should be located so that it does not interfere with or contact any sample vessels 28 when the pipette or sample probe 20 and the probe tip 12 are lowered into the sample vessel 28.

In a particular application for measuring HIL in blood sera, the plurality of fiber optic bundles 15 can be four in number; although the number can be more or less depending on a particular use. To keep the dimension of the device 10 to a minimum, the fiber optic bundles 15 can be fused together and/or can be collectively installed within a conduit (not shown). Such a conduit is, preferably, optically opaque.

One of the four fiber optic bundles 15d is optically coupled to a light-emitting source 16. The fiber optic bundles 15d transmit light 26, which exits out of the end 19 of the fiber optic bundle 15d. The emitted light is adapted to travel through the serum sample 29 in the cutaway portion 11, towards the light-reflecting surface 14 submerged therein.

Each of the other three fiber optic bundles 15a, 15b, and 15c is adapted to collect reflected light 27 from the light-reflecting surface 14. One or a plurality of light filters 17 and one or a plurality of light-intensity measuring devices 18 are optically coupled to a corresponding fiber optic bundle 15. Each light filter 17a, 17b, 17c corresponding to a discrete one of the three fiber optic bundles 15a, 15b, 15c can be a monochromatic or band-pass-type filter that is adapted to filter out light wavelengths except the optimal wavelengths corresponding to the maximum absorption of one of hemoglobin, bilirubin, and triglycerides.

A corresponding light-intensity measuring device 18a, 18b, and 18c, e.g., a photodiode, a phototube, a photomultiplier tube, and the like, is optically coupled to each of the fiber optic bundles 15a, 15b, and 15c. Light intensity-measuring devices 18 are adapted to measure the intensity of the filtered, reflected light 27 and to output data signals commensurate therewith.

The output data signals are transmitted to a processing device 13. The processing device 13 can be a hardwired device or a processor or microprocessor that is capable of running an algorithm, software, driver program, and the like. The processing device 13, in turn, is adapted to receive the output data signals; store the data as required; and to use the data to determine whether or not the levels of HIL for each blood serum sample exceeds pre-established threshold or acceptable hemoglobin, bilirubin, and triglycerides levels. The sample vessels 28 containing serum samples with elevated levels of hemoglobin, bilirubin, and triglycerides can be flagged or removed from the analyzer automatically or manually.

Figure 3:
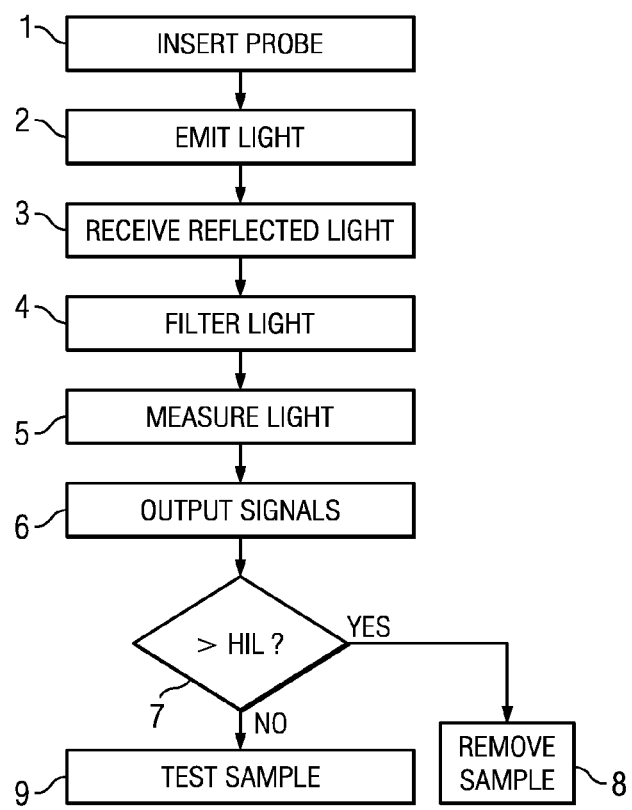
FIG. 3 is a flow chart of a method for measuring HIL in blood serum samples.

Having described a device for sampling and measuring HIL and for determining whether or not there are elevated levels of hemoglobin, bilirubin, and triglycerides in said samples, methods of measuring HIL in blood serum samples on an automated, clinical chemistry analyzer and of determining whether or not there are elevated levels of hemoglobin, bilirubin, and triglycerides in said serum samples will now be described. FIG. 3 shows a flow chart of an illustrative method.

During operation, the tip 12 of a clean, test or measuring probe 10 is inserted sufficiently, i.e. immersed, into a serum sample 29 (STEP 1) so that some of the blood serum 29 fills the cutaway portion 11. Once the probe tip 12 is sufficiently submerged, the light-emitting source 16 optically coupled to one of the fiber optic bundles 15d emits light that travels across the fixed path length of the cutaway portion 11 before the emitted light 26 is incident on and reflected by the light-reflecting surface 14 (STEP 2). Each of the other three fiber optic bundles 15a, 15b, and 15c is adapted to collect the reflected light 27 (STEP 3).

The collected, reflected light travels through the fiber optic bundles 15a, 15b, and 15c where it is filtered at discrete wavelengths (STEP 4) by light filters 17a, 17b, and 17c. As previously mentioned, each of the light filters 17 can be a band-pass filter that filters out reflected light at wavelengths that are close to the optimum wavelength associated with one of hemoglobin, bilirubin, and triglycerides. Subsequently, the intensity of the filtered, reflected light is measured, e.g., by light intensity-measuring devices 18a, 18b, and 18c (STEP 5). The light intensity-measuring devices 18a, 18b, and 18c generate output data signals commensurate with the measured wavelength intensity (STEP 6), which is transmitted to the processing device 13.

The processing device 13 receives the output data signals from the photodiodes and compares the HIL measurements with pre-established hemoglobin, bilirubin, and triglycerides threshold levels (STEP 7). If one or more of the HIL measurements exceeds the pre-established hemoglobin, bilirubin, and triglycerides threshold levels, then the sample vessel can be flagged or removed (STEP 8). Otherwise, the blood serum sample can be assayed (STEP 9) in accordance with the assay protocol with a high degree of assurance that the accuracy of the assays are not compromised due to elevated levels of HIL.

Although preferred embodiments of the invention have been described above, it will be recognized and understood that various modifications may be made in the invention and that the appended claims are intended to cover all such modifications which fall within the spirit and scope of the invention.

What I claim is:

1. A blood serum screening device for use with an automated, clinical chemistry analyzer, the device comprising:
    a plurality of fiber optic bundles, each having a first end and a second end;
    a light-reflecting mirror surface that is disposed at a distal end of the device;
    a support element supporting the plurality of fiber optic bundles and the light-reflecting mirror and maintaining each one of the first ends of the plurality of fiber optic bundles in fixed, spaced relation with respect to the light-reflecting mirror surface, the light-reflecting mirror surface positioned such that light emitted from the first end of a first one of the plurality of fiber optic bundles is reflected to the first end of a plurality of other ones of the plurality of fiber optic bundles; and
    a light-emitting source optically coupled to the second end of the first one of the plurality of fiber optic bundles and operative to cause light to be:
        emitted from the first end of the first one of the fiber optic bundles so as to pass through at least a portion of a serum sample when the light-reflecting mirror surface and the first ends of the plurality of fiber optic bundles are disposed therein;
        reflected from the light-reflecting mirror surface to the first end of the other ones of the plurality of fiber optic bundles, and
        emitted from the second end of the other ones of the plurality of fiber optic bundles;
    a plurality of light intensity measuring devices corresponding in number to the other ones of the plurality of fiber optic bundles;
    a plurality of light filters each having a substantially discrete filter wavelength and being disposed between the second end of one the other ones of the plurality of fiber optic bundles and one of the plurality of light intensity measuring devices such that filtered light from each of the plurality of light filters impinges upon a different one of the plurality of light intensity measuring devices;
    wherein
        each light intensity-measuring device is operative to produce an output data signal indicative of an intensity of the filtered light at the respective substantially discrete filter wavelength impinging upon the respective light intensity measuring device.

2. The device as recited in claim 1, further including a hydrophilic material disposed on at least the first ends of the plurality of fiber optic bundles and the light-reflecting mirror surface.

3. The device as recited in claim 1 further including a sample probe, wherein the support element is fixedly coupled to the sample probe of the automated, clinical chemistry analyzer.

4. The device as recited in claim 1, wherein the other ones of the plurality of optical fiber bundles include at least three other optical fiber bundles and the plurality of light filters are in optical communication with the second end of respective other optical fiber bundles and include:
    a first filter adapted to filter out light except for the optimal absorption wavelengths associated with hemoglobin;
    a second filter adapted to filter out light except for the optimal absorption wavelengths associated with bilirubin; and
    a third filter adapted to filter out light except for the optimal absorption wavelengths associated with triglycerides.

5. The device as recited in claim 1, wherein the each light intensity-measuring device is selected from the group comprising a photometer, a photodiode, a phototube or a photomultiplier tube.

6. The device as recited in claim 1 further comprising a processing device that is operative:
    to receive the output data signal from each of the light intensity-measuring devices;
    to compare each output data signal to a corresponding pre-established, acceptable intensity level threshold; and
    to provide an indication of whether one or more of the output data signals exceeds the corresponding pre-established, acceptable intensity level threshold.

7. The device as recited in claim 1, wherein the device is operationally coupled to a robotic arm of the automated, clinical chemistry analyzer.

8. The device as recited in claim 1, wherein the plurality of fiber optic bundles is at least one of fused together or collectively confined within a conduit.

9. An automated, clinical chemistry analyzer having the blood serum screening device as recited in claim 1.

10. The device as recited in claim 1 wherein the support element is removably coupled to the sample probe of the automated, clinical chemistry analyzer.

11. The device as recited in claim 1 wherein the light-reflecting mirror surface is spaced from the first ends of the plurality of fiber optic bundles by a few millimeters.

12. A method for measuring levels of hemoglobin, bilirubin, and triglycerides and for determining whether the measured levels exceed pre-established levels for each of hemoglobin, bilirubin, and triglycerides, the method comprising:
    providing an automated, clinical chemistry analyzer having the blood serum sampling device as recited in claim 1;
    immersing at least a portion of the support element in a blood serum sample such that at least a portion of the blood serum sample fills a space between the light-reflecting surface and the first ends of the plurality of fiber optic bundles;
    activating the light-emitting source to cause light to be:
    emitted from the first end of the first fiber optic bundle;
    transmitted through the blood serum sample to the light-reflecting mirror surface and to be reflected from the light-reflecting mirror surface through the blood serum sample toward the first ends of the other ones of the plurality of fiber optic bundles, the first ends of the other ones of the plurality of fiber optic bundles being positioned and operative to receive reflected light from the light-reflecting mirror surface such that light received at the first end of each of the other ones of the plurality of fiber optic bundles is emitted from the second end of each of the other ones of the plurality of fiber optic bundles;

filtering the light emitted from the second end of each of the other ones of the plurality of fiber optic bundles with a different one of the plurality of light filters to provide filtered light at each of the discrete filter wavelengths;

measuring an intensity of the filtered light at each of the discrete filter wavelengths with a light intensity measuring device, wherein the intensity of the filtered light at each of the filter wavelengths is associated with a level of hemoglobin, bilirubin and triglycerides, respectively in the blood serum sample;

comparing the measured intensity of the filtered light at each of the discrete filter wavelengths to pre-established intensity threshold levels for each of hemoglobin, bilirubin, and triglycerides; and providing an indication if the measured intensity of the filtered light at one or more of the discrete filter wavelengths exceeds the respective pre-established intensity threshold level.

13. The method as recited in claim 12 further comprising flagging, removing or discounting any blood serum sample having elevated levels from the pre-established levels for each of hemoglobin, bilirubin, and triglycerides.

14. The method as recited in claim 12 further comprising assaying the blood serum sample in the event the measured intensity of the filtered light at each of the discrete filter wavelengths is below the respective pre-established intensity threshold level for each of hemoglobin, bilirubin, and triglycerides.

15. The method as recited in claim 12 further comprising applying a hydrophilic material to at least the first ends of the plurality of fiber optic bundles and the light-reflecting mirror surface.

16. The method as recited in claim 12, wherein filtering the reflected light at discrete absorption wavelengths includes using at least one of a monochromatic filter and a band-pass filter.

17. The method as recited in claim 12, wherein filtering the reflected light includes:
  filtering out light except for the optimal absorption wavelengths associated with hemoglobin with a first light filter;
  filtering out light except for the optimal absorption wavelengths associated with bilirubin with a second light filter; and
  filtering out light except for the optimal absorption wavelengths associated with triglycerides with a third light filter.

18. A method for measuring levels of hemoglobin, bilirubin, and triglycerides in a blood serum sample and for determining whether the measured levels exceed pre-established threshold levels for one or more of hemoglobin, bilirubin, and triglycerides, the method comprising:
  fixedly-spacing first ends of a plurality of fiber optic bundles from a light-reflecting mirror surface in light-reflecting confronting relation, wherein the plurality of fiber optic bundles includes a first one of the plurality of fiber optic bundles and a plurality of other ones of the plurality of fiber optic bundles and wherein each one of the plurality of fiber optic bundles includes the first end and a second end;
  immersing the light-reflecting mirror surface and the first ends of the plurality of fiber optic bundles in the blood serum sample so that a portion of the blood serum sample fills a space between the first ends of the plurality of fiber optic bundles and the light-reflecting mirror surface, the first ends of plurality of fiber optic bundles and the light reflecting mirror surface being configured so that light emitted from the first end of the first one of the plurality of fiber optic bundles passes through at least the portion of the blood serum sample and is reflected from the light-reflecting mirror surface toward the first ends of the other ones of the plurality of fiber optic bundles;
  activating a light-emitting source coupled to the second end of the first one of the plurality of fiber optic bundles to cause light to be emitted from the first end of the first one of the plurality of fiber optic bundles; and
  receiving at the first end of each of the other ones of the plurality of fiber optic bundles, light emitted from the first end of the first one of the plurality of fiber optic bundles and reflected off of the light reflecting mirror surface toward the first ends of the other ones of the plurality of fiber optic bundles, so that light received at the first end of each of the other ones of the plurality of fiber optic bundles is emitted from the second end of each of the other ones of the plurality of fiber optic bundles;
  filtering the light emitted from the second end of each of the other ones of the plurality of fiber optic bundles with a corresponding light filter having a substantially unique discrete wavelength associated with hemoglobin, bilirubin and triglycerides, respectively, to produce filtered light at substantially each of the discrete wavelengths;
  measuring, an intensity of the filtered light at substantially each of the discrete wavelengths;
  comparing the measured intensity of the filtered light at substantially each of the discrete wavelengths to pre-established intensity threshold levels for hemoglobin, bilirubin, and triglycerides respectively; and
  providing an indication if the measured intensity of the filtered light at one or more of the substantially discrete wavelengths exceeds the respective pre-established intensity threshold level.

19. The method as recited in claim 18 further comprising applying a hydrophilic material to the first ends of the plurality of fiber optic bundles and to the light-reflecting mirror surface.

20. The method as recited in claim 18, wherein the filtering step includes performing the filtering using at least one of a monochromatic filter and a band-pass filter.

21. The method as recited in claim 18, wherein the filtering step includes:
  filtering out light except for the optimal absorption wavelengths associated with hemoglobin with a first light filter;
  filtering out light except for the optimal absorption wavelengths associated with bilirubin with a second light filter; and
  filtering out light except for the optimal absorption wavelengths associated with triglycerides with a third light filter.

* * * * *